United States Patent [19]

Kudla

[11] Patent Number: 5,203,653
[45] Date of Patent: Apr. 20, 1993

[54] REAMER FOR SHAPING BONE SOCKETS

[75] Inventor: John W. Kudla, Colonia, N.J.

[73] Assignee: Pfizer Hospital Products Group, Inc., New York, N.Y.

[21] Appl. No.: 814,137

[22] Filed: Dec. 30, 1991

[51] Int. Cl.[5] .................. A61B 17/32; A61B 17/18
[52] U.S. Cl. ................................. 408/207; 407/63; 408/227; 606/81
[58] Field of Search .................... 606/79-81, 606/84-89; 408/207, 227; 407/53, 54, 60-63

[56] References Cited

U.S. PATENT DOCUMENTS 2,785,673  3/1957  Anderson ............ 606/81 X
4,131,116  12/1978 Hedrick ............. 408/227 X Primary Examiner—Steven C. Bishop
Attorney, Agent, or Firm—Peter C. Richardson; Lawrence C. Akers; Raymond W. Augustin

[57] ABSTRACT

A reamer for shaping a socket, such as a hip socket, comprising a cutter head located at one end of a rotatably driven shaft and having a hemispherical portion with a hemispherical exterior surface, the hemispherical portion containing a closed hollow chamber, and helical openings, such as slots, in said hemispherical portion connecting between the exterior surface and the chamber, the trailing portion of each of the openings having a cutting edge raised slightly above the hemispherical surface to move material from the socket into the chamber during rotation of the cutter head, and an attachment element for connecting and disconnecting the cutter head and the drive shaft.

8 Claims, 3 Drawing Sheets

REAMER FOR SHAPING BONE SOCKETS

BACKGROUND OF THE INVENTION

1. Field of the Invention

This invention relates to a reamer for shaping bone sockets which has improved cutting characteristics. More particularly, the invention relates to a hemispherical reamer for shaping acetabulum.

2. Description of the Prior Art

Power driven reamers or bone cutters are utilized to round out and reshape the acetabular cavity or socket of the hip, following the destruction of cartilage or bone at the hip socket. Such power driven bone cutters utilize a plurality of blades having the cutting edges projecting slightly from the rotary hemispherical head of the cutter. In U.S. Pat. No. 3,633,583 to Meyer Fishbein dated Jan. 11, 1972, there is shown a substantially hemispherical head in which a single surgical blade is so shaped as to provide two radially disposed cutting edges on opposite sides of the rotational center line of the head. The edges project just slightly above the adjustment substantially hemispherical surface of the cutting head and the cutting edges are beveled in opposite directions on opposite sides of the axis of rotation so that both edges will cut during rotation of the head. Troughs or grooves are formed in the head forward of the cutting edges to transport the cut material from the surface of the head to the back end of the head. U.S. Pat. No. 4,621,637, also to Meyer Fishbein, relates to a hollow acetabular reamer having three radial cutting blades. The blades have slots adjacent thereto to allow debris to fall within the cup.

An additional bone cutter is disclosed in U.S. Pat. No. 4,131,116 which relates to a hemispherical shaped cutter head with a plurality of radial cutter slots passing from the exterior surface of the cutter head into a hollow chamber within the head. At the trailing side of each slot is formed a cutting edge which projects slightly above the surface of the cutter head. Each cutter edge extending beyond the surface of the head removes a small portion of bone or cartilage from the hip socket and this bone passes through the slot forward of the cutting edge into the head chamber where it is retained until the head is removed from the drive shaft. Thus, with this type of cutter head there is no loose bone or cartilage in the vicinity of the hip socket during rotation of the cutter head. By using at least three slots and cutting edges, the head is equally loaded during rotation in all radial directions so that there is no tendency for tipping of the axis of rotation of the head as the cutting operation proceeds. The cutting edges and slots of U.S. Pat. No. 4,131,116 are so formed in the head that at least one slot and cutting edge passes over the point at which the end of the axis of rotation intersects the cutter head so that the complete surface of the hip socket is removed. However, in cases where it is desired to leave a flat portion at the bottom of the socket, all of the slots and cutting edges will terminate short of the point at which the axis of rotation intersects the head.

The present invention is an improved version of the cutting head of U.S. Pat. No. 4,131,116. The cutting head of the present invention has superior cutting ability by providing a reamer having a cutting head containing helical slots and cutting edges which move the scrapings and bone cuttings into a normally sealed hollow chamber in the cutter head during rotation of the head. Thus, the cuttings cannot escape into the operating area until such time as the power drive is stopped and the head is removed for cleaning. Furthermore, by the use of at least three helical cutting blades, the maintenance of the axis of cutting is more easily assured and by providing a quick disconnect of the cutter head from the drive shaft, it is possible to easily change the size of the cutter head to enlarge the size of the hip socket.

The use of helical slots produces more efficient cutting in that bone or tissue is sliced rather than scraped off, as is the case with radial slots. The proper rake cutting angle and helical slot angle produce lower temperature cutting and can be varied to cut more or less aggressively. A positive rake angle is used to ensure that the cutting edges are pulled into the material to be cut.

SUMMARY OF THE INVENTION

It is an object of the invention to provide a reamer for use in preparing acetabulum to receive a prosthetic implant which has efficient cutting characteristics and generates little heat during cutting.

It is a further object of this invention to provide a hemispherically-shaped reamer having at least three slots extending across the surface thereof in a plane extending at a predetermined angle with respect to the polar axis of the hemisphere.

Accordingly, these and other objects of the invention are provided by a reamer for shaping an acetabular socket which includes a hemispherical cutting head having a hollow interior. The cutting head has a plurality of slots formed therein with the slots converging towards the polar region on the hemispherical cutting head. The pole on the hemisphere is defined by the polar axis of the hemisphere with at least one slot extending across this polar region to ensure complete cutting across the entire surface of the cutting head. The slots extend across the hemispherical cutting head in planes oriented at a predetermined angle to the polar axis of the cutting head. Each slot has a trailing cutting edge having a radius from the center of the hemisphere greater than the radius to the leading edge of the slot. The slicing action of the helical slots in the hemispherical cutting head allows the material to be cut efficiently and be moved into the hollow interior of the socket during rotation thereof to be accumulated for use as bone graft material.

In the preferred embodiment, the predetermined angle of the plane containing the slots to the polar axis is 40°. In general, this may range from 30° to 40° depending on the aggressiveness of the cutting desired, with 40° being more aggressive. While in the preferred embodiment there are 6 helical slots spaced at 60°, less than 6 slots are also possible. For example, 3 slots may be used spaced 120° apart.

In order to improve reaming efficiency, the exterior surface of the hemispherical cup in the area adjacent the trailing edge of each slot may be relieved by removing material so that the area immediately trailing the cutting edge has a radius of between 0.005" and 0.025" less than the radius of the trailing edge, that is, the cutting edge of each slot. Alternately, a 15° relief angle can be cut in the material trailing the cutting edge of each slot.

These and other objects and advantages of the present invention will become apparent from the following description of the accompanying drawings, which disclose one embodiment of the invention. It is to be understood that the drawings are to be used for purposes of illustration only, and not as a definition of the invention.

BRIEF DESCRIPTION OF THE DRAWINGS

In the drawings, wherein similar reference characters denote similar elements throughout the views.

DETAILED DESCRIPTION OF THE INVENTION

Referring to FIGS. 1-6 there is shown a reamer generally denoted as 10 for shaping a bone socket and in particular, an acetabular socket prior to implantation of a prosthetic acetabulum (not shown). The reamer is composed of a hollow hemispherical cutting head 12 containing a plurality of slots 14. In the preferred embodiment there are 6 slots spaced at 60° around the circumference of the hemispherically shaped cutting head 12. While 6 slots 14 are shown, 3 slots spaced at 120° may also be utilized.

In the preferred embodiment slots 14 are included with respect to the polar axis 40 of hemispherical cutting head 12 at an angle of preferably between 30° and 40°, and always between 20° and 50°.

Figure 3:
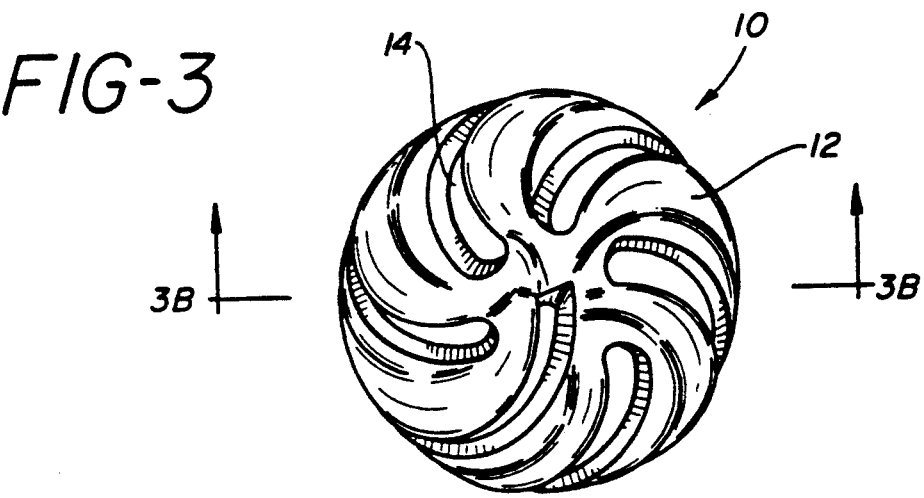
FIG. 3 is a plan view of the cutting head shown in FIG. 1.
Figure 3B:
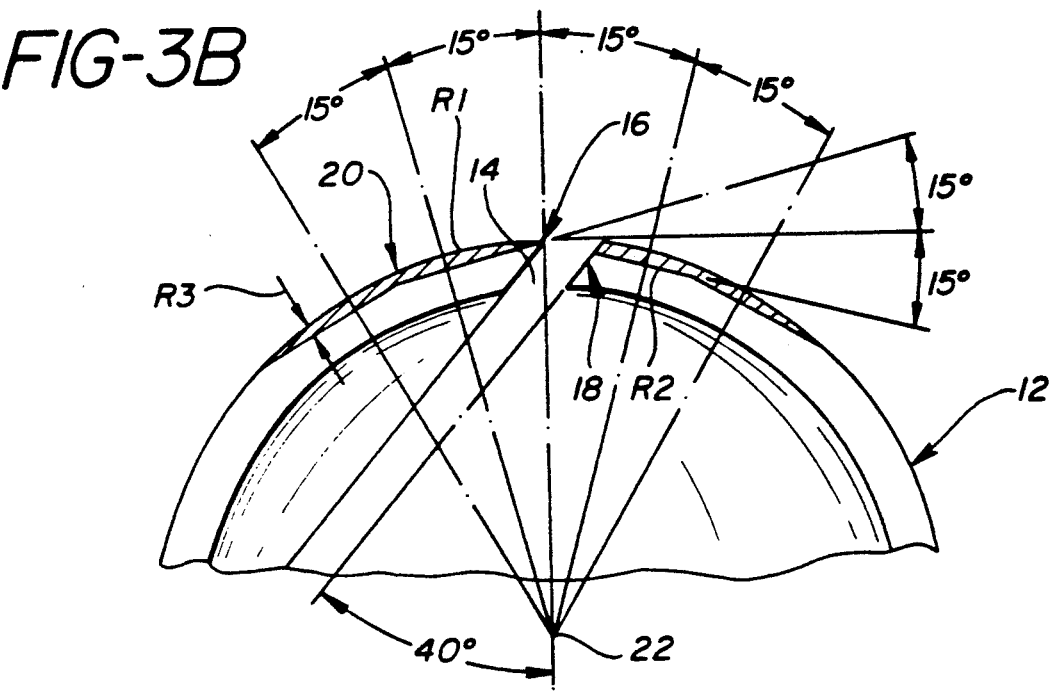
FIG. 3B is a cross-sectional view of the cutting head shown in FIGS. 3 along lines 3B—3B.
Figure 4:
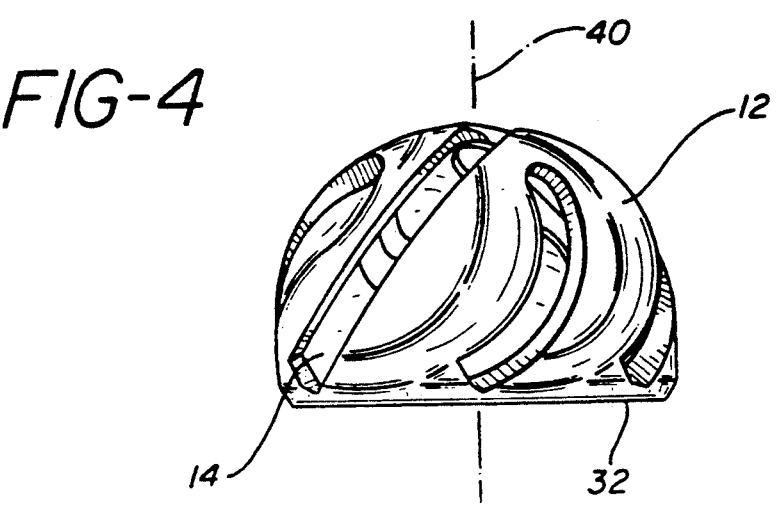
FIG. 4 is a side elevation view of the cutting head shown in FIG. 1.

As best seen in FIG. 3B, each slot 14 includes a trailing edge 16 and a leading edge 18. Trailing edge 16, which forms the cutting edge, extends at a radius R1 from center 22 of hemispherical cutting head 12, which radius is greater than the radius R2 at which the leading edge 18 of the outer surface of cutting head 12 extends from the center 22. However, the radius of the leading edge is relieved by cutting off between 0.005" and 0.025" by tilting the cutter head during fabrication so that the leading edge 18 is below cutting edge 16.

In the preferred embodiment, the area 20 immediately trailing the trailing edge 16 also includes a relief R3 to allow for the more efficient cutting of the tissue or bone. In the preferred embodiment, this relief is between 0.005" and 0.025" and may be cut at an angle of 15° radially inwardly from the tangent at point 16.

Figure 5:
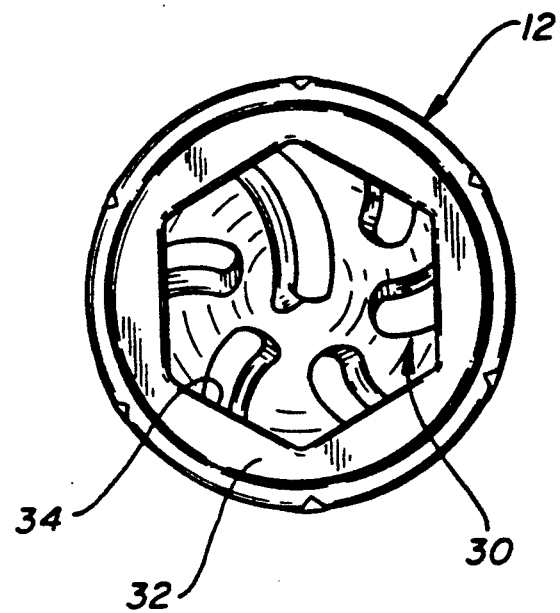
FIG. 5 is a bottom plan view of the cutting head shown in FIG. 1.

Referring to FIG. 5 there is shown the bottom plan view of the cutting head 12 showing hollow interior portion 30 and bottom flange 32. In the preferred embodiment, flange 32 includes a hexagonal opening 34 which rotates the reamer via a drive shaft and power driver (not shown).

Figure 6:
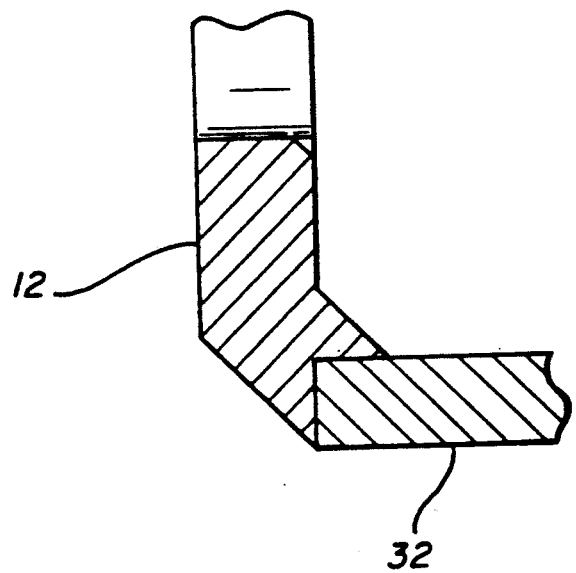
FIG. 6 is an enlarged cross-sectional view taken along the lines 6—6 of FIG. 2 showing the preferred assembly of the base plate to the hemispherical cutting portion of the cutting head.

Referring to FIG. 6 there is shown one method of forming cutting head 12. In this method, bottom flange 32 is assembled to the hemispherical portion of cutting head 12 and shrunk fit or welded thereto. Flange 32 may include any well known means to connect cutting head 14 to a shaft of the driver. Shown is a hexagonal opening to receive a hex head drive, but any other mating structure can be used.

Figure 1:
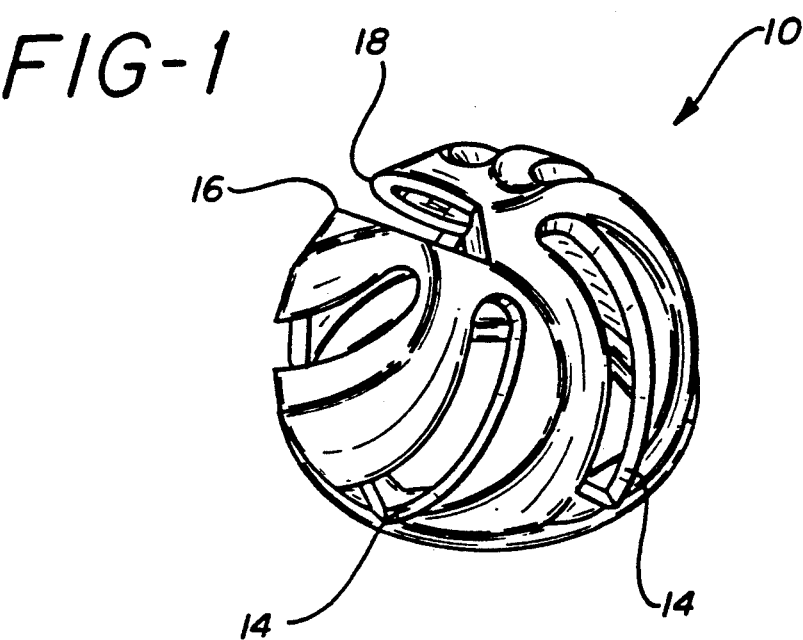
FIG. 1 is an isometric view of the hemispherical cutting head of the present invention including 6 helical slots formed therein.
Figure 2:
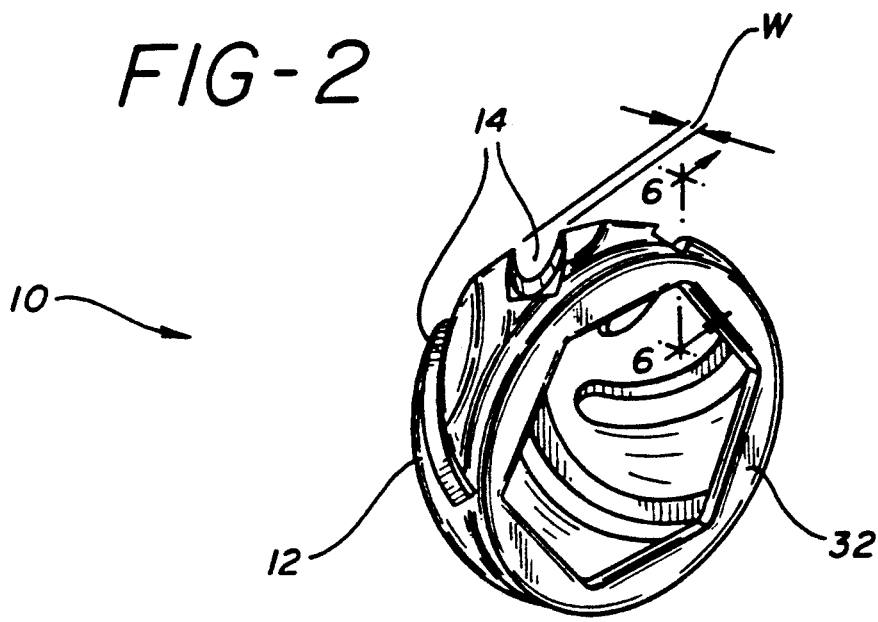
FIG. 2 is an isometric view of the cutting head shown in FIG. 1 in a position allowing the hollow interior to be exposed.

Reamers 10 may be supplied in various sizes, for example, ranging from 26 mm in diameter to 32 mm in diameter, all having at least three slots 14. It has been found that with this size diameter cutting head that slot widths W, as shown in FIG. 2, are preferably 0.125". It has also been found that a positive rake angle aids the cutting action by drawing the cutting head into the material being cut with this rake angle being equal to the angle of the plane containing slots 14, i.e. between 30° and 40°.

The preferred method of forming the slots in the hemispherical cutting head of the present invention is to use a T-shaped slot cutter (not shown) in which the cross-bar of the T is circular with teeth around its circumference. The long shaft of the T is oriented vertically in a vertical boring mill. Cutting head 12 is mounted on a fixture which may be indexed in 15° increments around a polar axis which is inclined to the vertical. In the preferred embodiment, the polar axis 40 of the cutting head is inclined at 40° with respect to the vertical axis of the T-slot cutter and then the cutter is moved into contact with the outer spherical surface of cutting head 12 to form slot 14. The cutting head 12 is then indexed in the inclined position 60° to form 6 slots (120° to form 3 slots) and the remaining slots are cut in a like manner. One slot extends beyond the center point on the outer surface of head 14 by approximately 0.065" to ensure that a cutting edge extends across the entire circumference of hemispherical cutting head 12.

After the slots are cut, a straight side cutting end mill is inserted in the vertical boring mill to cut the 15° relief. The cutter 12 is indexed at 15° increments and the end mill cuts a relief along a circumferential arc (i.e. rotate cutting head 12 to allow the mill to cut the relief). After the relief is cut, the cutting edge is above the relief angle cut on the leading edge.

While several examples of the present invention have been described, it is obvious that many changes and modifications may be made thereunto, without departing from the spirit and scope of the invention.

I claim:

1. A reamer for shaping a socket comprising:
    a cutting head comprising a hemispherical portion having a hemispherical exterior surface and containing a hollow chamber;
    at least three elongate helical slots each extending along a single plane oriented at a predetermined angle between 20° and 50° to the polar axis of said hemispherical portion between said hemispherical exterior surface and said chamber, said slots converging toward the center point of said hemispherical exterior surface but being unconnected to each other at said point; and
    a cutting edge on the trailing portion of each of said slots and raised slightly above said hemispherical exterior surface of said hemispherical portion for moving material from said socket into said chamber during the rotation of said reamer.

2. The reamer as set forth in claim 1 wherein said predetermined angle is 40°.

3. The reamer as set forth in claim 1 wherein said slots are six in number and are spaced 60° around the exterior surface of said cutting head.

4. The reamer as set forth in claim 1 wherein said slots are three in number and are spaced one hundred and twenty degrees apart around the exterior surface of said cutting head.

5. The reamer as set forth in claim 1 wherein one of said slots extending across the point of intersection of the rotating axis of said shaft with said hemispherical portion, the cutting edge on said one slot adapted to remove the bottom of said socket upon rotation of said cutter head.

6. A reamer for shaping a socket comprising:
a hemispherical cutting head having a hollow interior and having a plurality of slots formed therein, said slots converging towards the central pole on said hemispherical cutting head defined by the polar axis of said cutting head, each of said slots extending across said hemispherical cutting head along a single planes oriented at a predetermined angle of between 20° and 50° to said polar axis and a cutting edge on a trailing of each of said slots having a radius from the center of said hemispherical cutting head greater than the radius of the leading edge of each slot for removing moving material from said socket into said hollow interior of said cutting during rotation thereof.

7. The reamer as set forth in claim 6 wherein said predetermined angle is 40°.

8. The reamer as set forth in claim 6 further including a cutting relief area trailing said trailing edge of said slot and having a radius between 0.005" and 0.025" less than the radius of said trailing edge.

* * * * *